United States Patent
Lin et al.

(10) Patent No.: US 7,887,834 B2
(45) Date of Patent: Feb. 15, 2011

(54) AQUEOUS DISPERSIONS OF SILICONE POLYETHER BLOCK COPOLYMERS

(75) Inventors: Shaow Lin, Midland, MI (US); Kimmai Nguyen, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 65 days.

(21) Appl. No.: 10/594,399

(22) PCT Filed: Apr. 19, 2005

(86) PCT No.: PCT/US2005/013328
§ 371 (c)(1),
(2), (4) Date: Sep. 26, 2006

(87) PCT Pub. No.: WO2005/103118
PCT Pub. Date: Nov. 3, 2005

(65) Prior Publication Data
US 2007/0219318 A1    Sep. 20, 2007

Related U.S. Application Data

(60) Provisional application No. 60/563,663, filed on Apr. 20, 2004, provisional application No. 60/611,258, filed on Sep. 17, 2004, provisional application No. 60/611,151, filed on Sep. 17, 2004, provisional application No. 60/611,229, filed on Sep. 17, 2004.

(51) Int. Cl.
*A61K 9/127* (2006.01)
(52) U.S. Cl. .................... 424/450; 424/70.12
(58) Field of Classification Search .......... 525/94
See application file for complete search history.

(56) References Cited

U.S. PATENT DOCUMENTS

| 2,823,218 | A |   | 2/1958  | Speler et al.   |         |
|-----------|---|---|---------|-----------------|---------|
| 3,957,842 | A |   | 5/1976  | Prokai et al.   |         |
| 4,122,029 | A |   | 10/1978 | Gee et al.      |         |
| 4,150,048 | A |   | 4/1979  | Schilling, Jr. et al. | |
| 4,886,068 | A | * | 12/1989 | Kaneko et al.   | 600/437 |
| 5,364,633 | A |   | 11/1994 | Hill et al.     |         |
| 5,387,417 | A |   | 2/1995  | Rentsch         |         |
| 5,393,452 | A |   | 2/1995  | Raleigh et al.  |         |
| 5,411,744 | A |   | 5/1995  | Hill et al.     |         |
| 5,472,686 | A |   | 12/1995 | Tsubaki et al.  |         |
| 5,478,860 | A |   | 12/1995 | Wheeler et al.  |         |

(Continued)

FOREIGN PATENT DOCUMENTS

EP         0598531         5/1994

(Continued)

OTHER PUBLICATIONS

J. Newton et al,: "Silicone-Based Vesicle Delivery Systems" Cosmetics & Toiletries, vol. 119, No. 12, 2004, pp. 53-60.

*Primary Examiner*—Randy Gulakowski
*Assistant Examiner*—Robert Loewe
(74) *Attorney, Agent, or Firm*—Alan Zombeck

(57) ABSTRACT

Aqueous dispersions of $(AB)_n$ silicone polyether block copolymers, methods for preparing the dispersion compositions, and personal, household, and healthcare formulations containing the compositions are disclosed. The aqueous dispersions can be either vesicle or emulsion compositions depending on the $(AB)_n$ silicone polyether block copolymers structure and method of preparing the dispersion.

1 Claim, 7 Drawing Sheets

Particle size distributions for vesicle compositions, Examples 14 - 16

U.S. PATENT DOCUMENTS

| | | | |
|---|---|---|---|
| 5,620,684 A | 4/1997 | Dupuis | |
| 5,623,017 A | 4/1997 | Hill | |
| 5,660,819 A * | 8/1997 | Tsubaki et al. | 424/70.1 |
| 5,660,853 A | 8/1997 | Hansenne-Richoux | |
| 5,705,562 A | 1/1998 | Hill | |
| 5,707,613 A | 1/1998 | Hill | |
| 5,741,518 A * | 4/1998 | Ribier et al. | 424/450 |
| 5,767,219 A | 6/1998 | Takarada et al. | |
| 5,811,487 A | 9/1998 | Schulz, Jr. et al. | |
| 5,869,727 A * | 2/1999 | Crane et al. | 556/445 |
| 5,919,487 A * | 7/1999 | Simonnet et al. | 424/490 |
| 5,925,341 A | 7/1999 | Cervantes et al. | |
| 5,948,855 A | 9/1999 | Lin et al. | |
| 5,958,433 A | 9/1999 | Simonnet | |
| 5,958,448 A * | 9/1999 | Ekeland et al. | 424/450 |
| 6,017,546 A | 1/2000 | Glover | |
| 6,039,936 A | 3/2000 | Restle et al. | |
| 6,120,778 A * | 9/2000 | Simonnet | 424/401 |
| 6,168,782 B1 | 1/2001 | Lin et al. | |
| 6,210,690 B1 | 4/2001 | Nabeshima et al. | |
| 6,562,356 B2 | 5/2003 | Verite et al. | |
| 6,632,420 B1 | 10/2003 | Cen et al. | |
| 6,831,128 B2 * | 12/2004 | Altes et al. | 524/806 |
| 6,902,722 B2 * | 6/2005 | Candau et al. | 424/59 |
| 6,916,774 B2 * | 7/2005 | Trinh et al. | 510/287 |
| 6,998,424 B2 | 2/2006 | Feng et al. | |
| 7,041,630 B1 * | 5/2006 | Trinh et al. | 510/287 |
| 2002/0086935 A1 | 7/2002 | Ferritto et al. | |
| 2003/0032717 A1 | 2/2003 | Ferritto et al. | |
| 2003/0040571 A1 * | 2/2003 | Feng et al. | 524/837 |
| 2003/0050393 A1 | 3/2003 | Ferritto et al. | |
| 2003/0119779 A1 | 6/2003 | Maxon et al. | |
| 2003/0171479 A1 * | 9/2003 | Lennon | 524/501 |
| 2003/0220425 A1 | 11/2003 | Ferritto et al. | |
| 2003/0224060 A1 * | 12/2003 | Simonnet et al. | 424/497 |
| 2004/0076652 A1 * | 4/2004 | Paspaleeva-Kuhn et al. | 424/401 |
| 2004/0077776 A1 | 4/2004 | Feng et al. | |
| 2004/0228821 A1 * | 11/2004 | Sunkel et al. | 424/70.12 |
| 2007/0166263 A1 | 7/2007 | Lin | |
| 2007/0217990 A1 | 9/2007 | Lin | |
| 2007/0219318 A1 | 9/2007 | Lin et al. | |
| 2007/0243241 A1 | 10/2007 | Lin et al. | |
| 2007/0256595 A1 | 11/2007 | Nozoe | |

FOREIGN PATENT DOCUMENTS

| | | |
|---|---|---|
| EP | 0483465 | 8/1995 |
| EP | 0523418 | 10/1996 |
| EP | 0724876 | 1/2000 |
| EP | 0780113 | 9/2002 |
| JP | 2000313808 | 11/2000 |
| WO | WO9906473 | 2/1999 |
| WO | WO0132146 | 5/2001 |
| WO | WO03010412 | 2/2003 |
| WO | WO03011948 | 2/2003 |
| WO | WO 03/101412 A2 | 12/2003 |
| WO | WO 2004/050045 A1 | 6/2004 |
| WO | WO 2005/102006 A1 | 11/2005 |
| WO | WO 2005/102248 A2 | 11/2005 |
| WO | WO 2005/103117 A1 | 11/2005 |
| WO | WO 2005/103157 A1 | 11/2005 |
| WO | WO2005103118 | 11/2005 |
| WO | WO2006028198 | 3/2006 |
| WO | WO2006091295 | 8/2006 |
| WO | WO2007053424 | 5/2007 |
| WO | WO2007100416 | 9/2007 |

* cited by examiner

Particle size distributions for vesicle compositions, Examples 14 - 16

(AB)n SPE 2 in water dispersion (AB)n SPE Block Copolymer Dispersion:
As Dispersed in 10 SPE /30EtOH / 60 Water (AB)n SPE Block Copolymer Dispersion:
Mixed, Homogenized in EtOH / Water

(AB)n SPE 1 Dispersion:
Stripped to Remove EtOH

Cryo-TEM image of body lotion of Example 29
formulated from vitamin-loaded SPE vesicles Cryo-TEM image of gel from Example 30
formulated from vitamin-loaded SPE vesicles

US 7,887,834 B2

AQUEOUS DISPERSIONS OF SILICONE POLYETHER BLOCK COPOLYMERS

CROSS REFERENCE TO RELATED APPLICATIONS

This application is a U.S. national stage filing under 35 U.S.C. §371 of PCT Application No. PCT/US05/013328 filed on 19 Apr. 2005, currently pending, which claims the benefit of U.S. Provisional Patent Application No. 60/563,663 filed 20 Apr. 2004, and U.S. Provisional Patent Application No. 60/611,258 filed 17 Sep. 2004, and U.S. Provisional Patent Application No. 60/611,151 filed 17 Sep. 2004, and U.S. Provisional Patent Application No. 60/611,229 filed 17 Sep. 2004 under 35 U.S.C. §119 (e). PCT Application No. PCT/US05/013328 and U.S. Provisional Patent Application No. 60/563,663, 60/611,258, 60/611,151, and 60/611,229 are hereby incorporated by reference.

FIELD OF THE INVENTION

This application relates to aqueous dispersions of $(AB)_n$ silicone polyether block copolymers, methods for preparing the dispersion compositions, and personal, household, and healthcare formulations containing the compositions. The aqueous dispersions can be either vesicle or emulsion compositions depending on the $(AB)_n$ silicone polyether block copolymers structure and method of preparing the dispersion.

BACKGROUND OF THE INVENTION

Silicone surfactants have been designed for various applications by combining a hydrophobic organopolysiloxane with various hydrophilic moieties. For example, the silicone surfactants known as silicone polyethers (SPEs) are based on copolymer structures of polyorganosiloxanes having pendant polyoxyalkylene groups. Most commonly, the copolymer structures of silicone polyethers are the "rake" type, where a predominately linear polyorganosiloxane provides the "backbone" of the copolymer architecture with pendant polyoxyalkylene groups forming the "rake". "ABA" structures are also common, where a pendant polyoxyalkylene group is at each molecular terminal of a linear polyorganosiloxane. $(AB)_n$ silicone polyethers are also known, wherein blocks of a siloxane units and polyether units repeat to form the copolymer. $(AB)_n$ SPEs are not as predominant in the art as the rake or ABA silicone polyethers. For example, there are numerous teachings describing various rake and ABA silicone polyethers structures for applications in many personal, household, and health care compositions as emulsifiers, wetting agents, and general-purpose aqueous surfactants. More recently, the aggregation behavior of rake and ABA silicone polyethers has been reported.

Long-standing needs in the field of cosmetic and drug formulation/delivery field are to identify vesicle compositions that form and entrap actives easily, are stable under various chemical and mechanical stresses, and yet are able to deliver the actives in a controlled manner under desired conditions. Vesicles derived from silicone surfactants, and more particularly silicone polyether surfactants, are of interest because of additional inherent benefits that this class of surfactants possesses vs. other types. For example, silicone polyether surfactants often have improved aesthetics in personal care formulations.

U.S. Pat. Nos. 5,364,633 and 5,411,744 by Hill teaches the self-assembly of silicone vesicles in aqueous dispersions of certain silicone polyethers. PCT application US03/38455 by Lin teaches the entrapment of various oils in silicone vesicles and their use in various personal care formulations.

The present inventors have discovered that certain $(AB)_n$ silicone polyethers form unique dispersions in aqueous media. In one embodiment, certain defined $(AB)_n$ SPE structures will form vesicle compositions in aqueous media. In a second embodiment, certain $(AB)_n$ SPE structures form stable dispersions that can be used to create emulsions. These stable dispersions and vesicles can be used to formulate compositions for the delivery of pharmaceutical and personal care actives.

While $(AB)_n$ silicone polyether block copolymers are known, the selection of the specific structures or certain molecular variables that enables the copolymers to form stable dispersions in aqueous media is heretofore unknown.

SUMMARY OF THE INVENTION

The present invention relates to aqueous compositions having dispersed particles wherein the dispersed particles comprise an $(AB)_n$ block silicone polyether copolymer having the average formula;

$$-[R^1(R_2SiO)_x(R_2SiR^1O)(C_mH_{2m}O)_y]_z-$$

where
x and y are greater than 4, m is from 2 to 4 inclusive, z is greater than 2,
R is independently a monovalent organic group,
$R^1$ is a divalent hydrocarbon containing 2 to 30 carbons.

The present invention further relates to a process for making an aqueous composition comprising;
I) combining,
  A) an $(AB)_n$ block silicone polyether copolymer having the average formula;

$$-[R^1(R_2SiO)_x(R_2SiR^1O)(C_mH_{2m}O)_y]_z-$$

where x and y are greater than 4, m is from 2 to 4 inclusive,
    z is greater than 2,
    R is independently a monovalent organic group,
    $R^1$ is a divalent hydrocarbon containing 2 to 30 carbons,
  B) an optional water miscible volatile solvent,
  with water to form an aqueous dispersion,
II) mixing the aqueous dispersion to form dispersed particles of the $(AB)_n$ silicone polyether copolymer having an average particle size of less than 10 micrometers,
III) optionally, removing the water miscible volatile solvent from the aqueous dispersion.

The present invention also provides a process for preparing a water continuous emulsion having an average particle size of less than 10 micrometers comprising;
I) mixing
  A) an $(AB)_n$ block silicone polyether copolymer having the average formula;

$$-[R^1(R_2SiO)_x(R_2SiR^1O)(C_mH_{2m}O)_y]_z-$$

where x and y are greater than 4, m is from 2 to 4 inclusive,
    z is greater than 2,
    R is independently a monovalent organic group,
    $R^1$ is a divalent hydrocarbon containing 2 to 30 carbons,
  B) a water miscible volatile solvent
  to form a hydrophobic phase,
II) adding water to the hydrophobic phase to form the water continuous emulsion.

Furthermore, the present invention relates to personal, household, and healthcare formulations containing the inventive aqueous compositions.

DETAILED DESCRIPTION OF THE INVENTION

Figure 1:
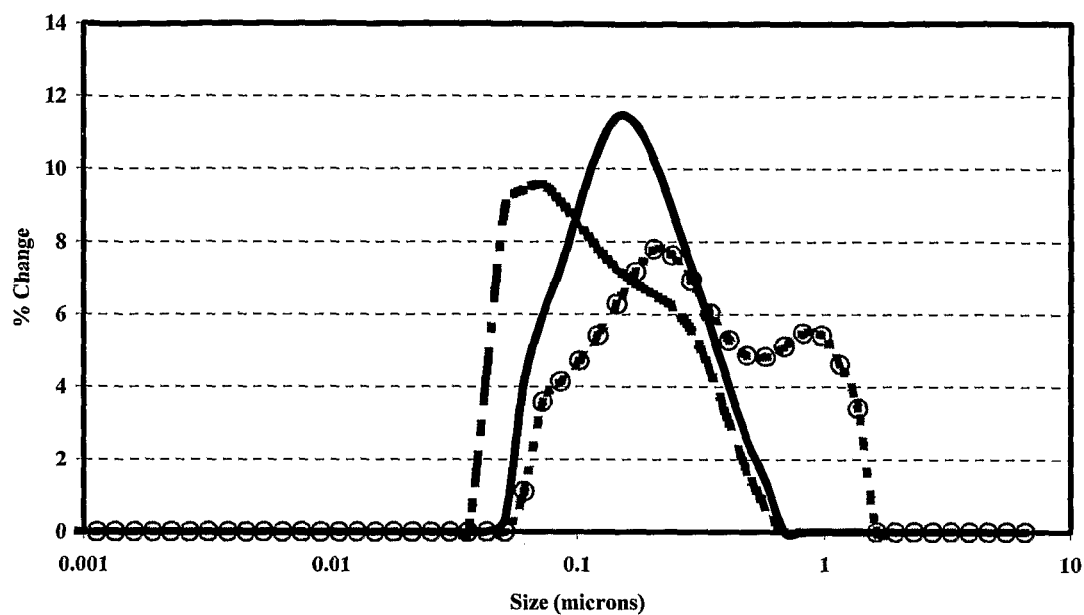
FIG. 1—Particle size distributions for vesicle compositions, Examples 14-16
FIG. 2—Cyro TEM of (AB)n SPE 2 in water dispersion
FIG. 3—Cyro TEM of (AB)n SPE Block Copolymer Dispersion; As Dispersed in 10 SPE/30 EtOH/60 Water
FIG. 4—Cyro TEM of (AB)n SPE Block Copolymer Dispersion in EtOH/Water
FIG. 5—Cyro TEM of (AB)n SPE 1 Dispersion; Stripped to Remove EtOH
FIG. 6—Cryo-TEM image of body lotion of Example 29, formulated from vitamin-loaded SPE vesicles
FIG. 7—Cryo-TEM image of gel from Example 30 formulated from vitamin-loaded SPE vesicles
Figure 2:
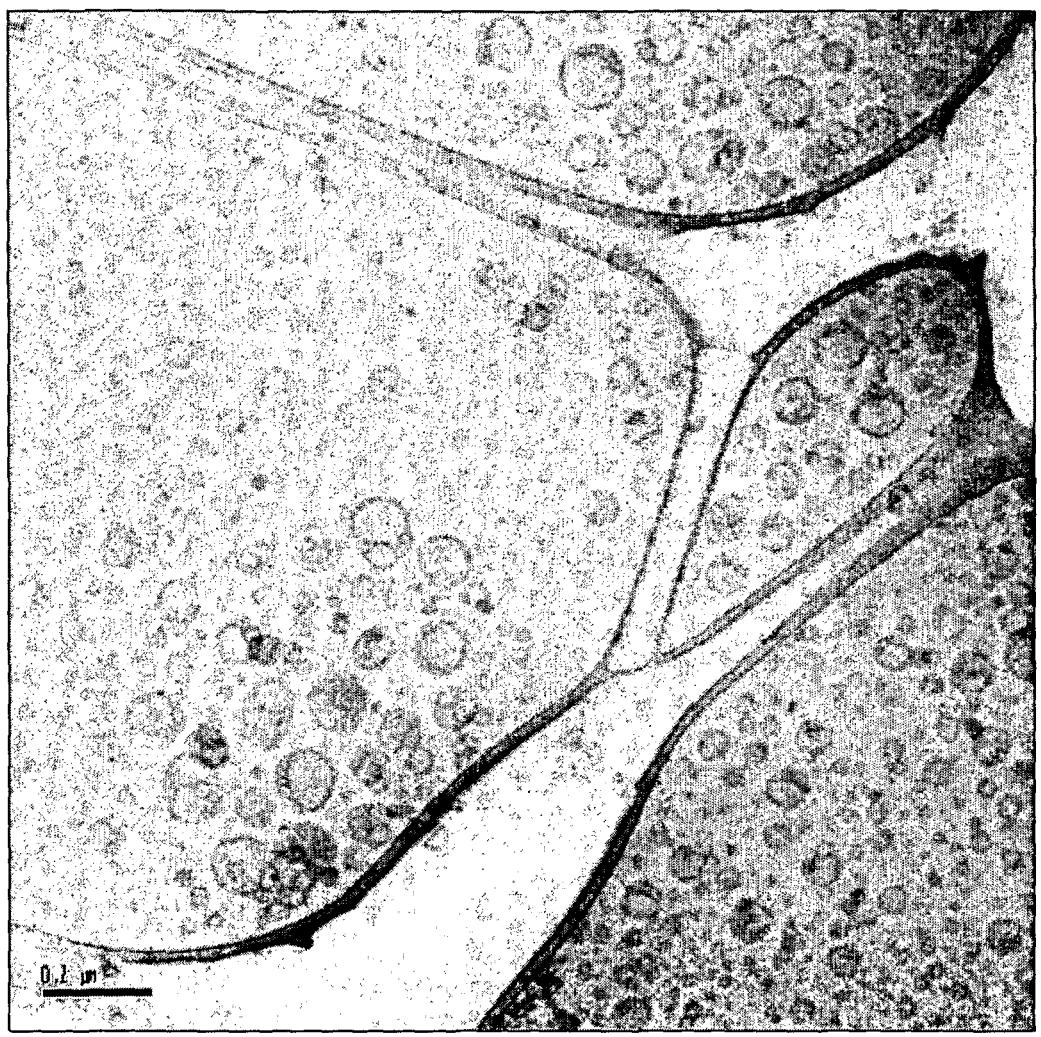
Figure 3:
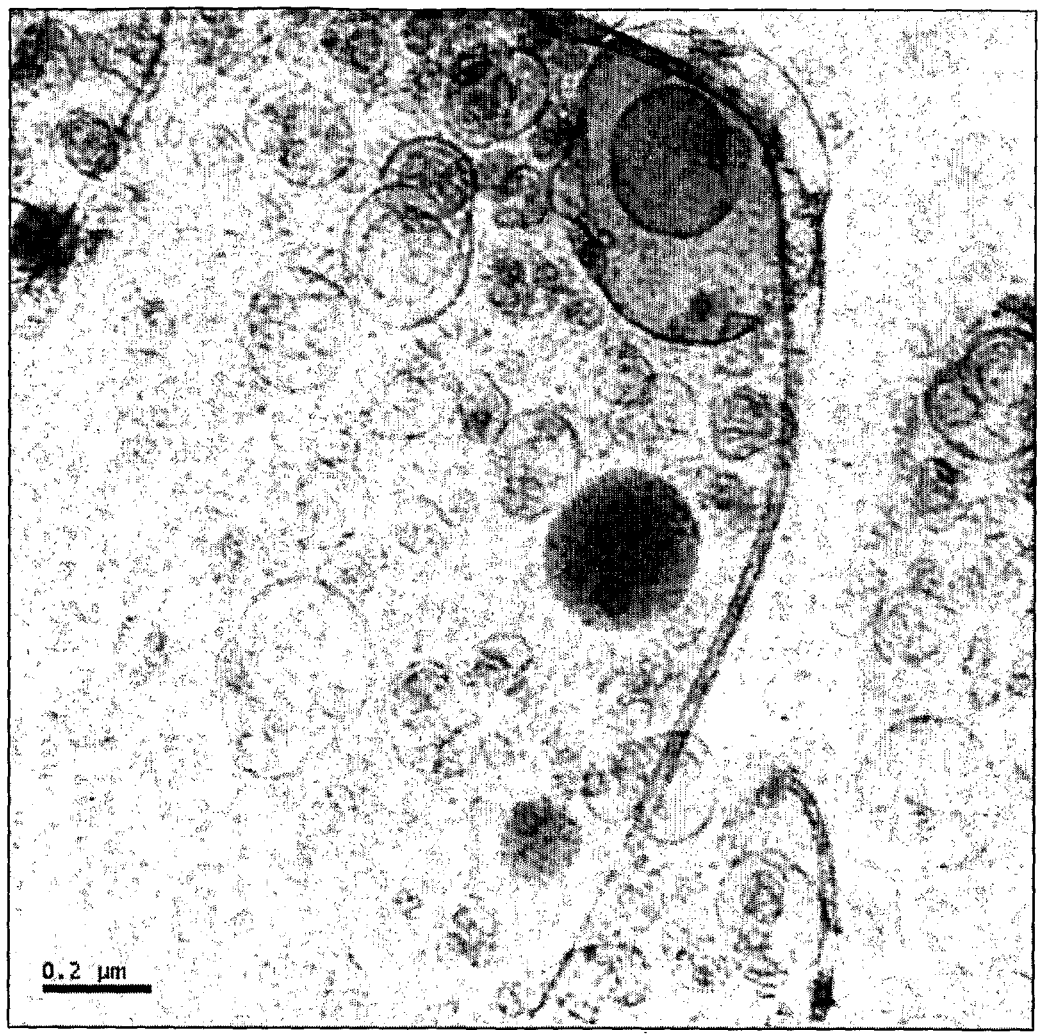
Figure 4:
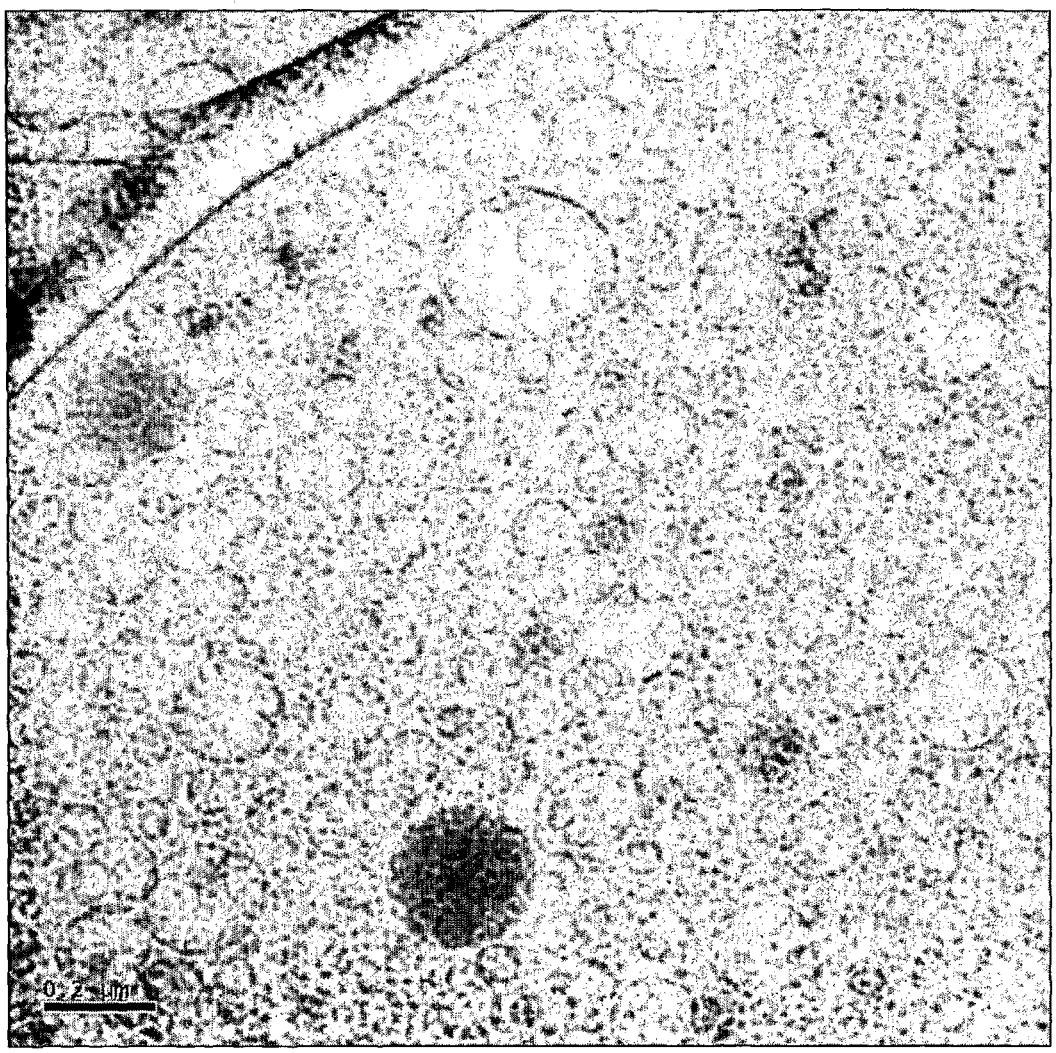
Figure 5:
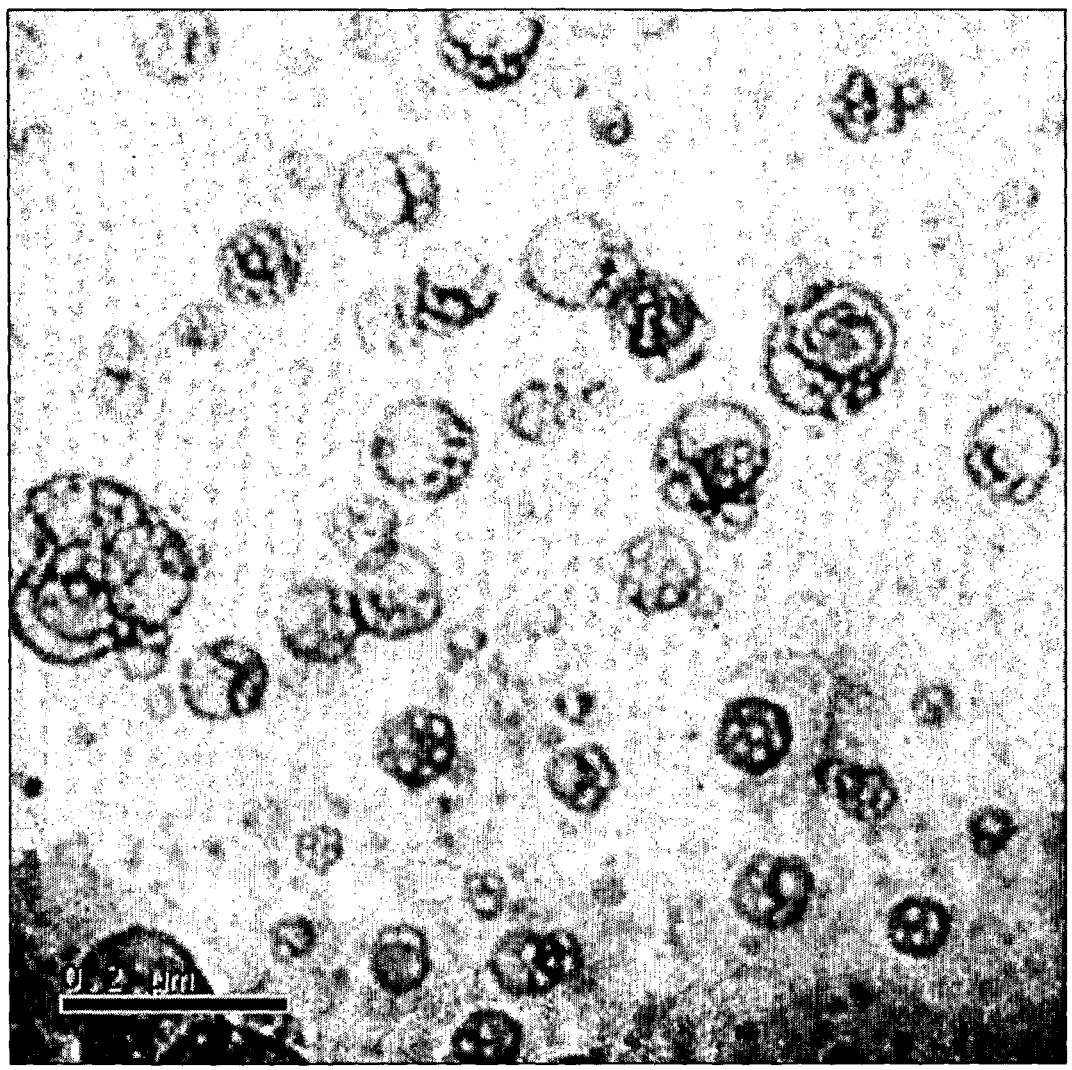

The present invention provides aqueous compositions having dispersed particles wherein the dispersed particles comprise an $(AB)_n$ block silicone polyether copolymer having the average formula;

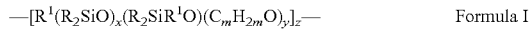  Formula I where
x and y are greater than 4, m is from 2 to 4 inclusive, z is greater than 2,
R is independently a monovalent organic group,
$R^1$ is a divalent hydrocarbon containing 2 to 30 carbons.

The siloxane block in Formula I is a predominately linear siloxane polymer having the formula $(R_2SiO)_x$, wherein R is independently selected from a monovalent organic group, x is an integer greater than 4. In a first embodiment the value of x (i.e. the degree of polymerization, DP, of the polysiloxane chain ranges from 20 to 100, alternatively from 30 to 75. These structures form vesicles in aqueous media, as discussed infra. In a second embodiment, the value of x ranges from 5 to 19, alternatively from 5 to 15. These structures form stable emulsions in aqueous media having a particle size of less than 10 micrometers, also discussed infra.

The organic groups represented by R in the siloxane polymer are free of aliphatic unsaturation. These organic groups may be independently selected from monovalent hydrocarbon and monovalent halogenated hydrocarbon groups free of aliphatic unsaturation. These monovalent groups may have from 1 to 20 carbon atoms, alternatively 1 to 10 carbon atoms, and are exemplified by, but not limited to alkyl groups such as methyl, ethyl, propyl, butyl, pentyl, hexyl, heptyl, octyl, undecyl, and octadecyl; cycloalkyl such as cyclohexyl; aryl such as phenyl, tolyl, xylyl, benzyl, and 2-phenylethyl; and halogenated hydrocarbon groups such as 3,3,3-trifluoropropyl, 3-chloropropyl, and dichlorophenyl. At least 50 percent, alternatively at least 80%, of the organic groups free of aliphatic unsaturation in the organopolysiloxane may be methyl (denoted as Me). Typically, the siloxane block is a predominately linear polydimethylsiloxane having the formula $(Me_2SiO)_x$, where x is as defined above.

The polyoxyalkylene block of the silicone polyether is represented by the formula $(C_mH_{2m}O)_y$, wherein m is from 2 to 4 inclusive, and y is greater than 4, alternatively y can range from 5 to 45, or alternatively from 5 to 25. The polyoxyalkylene block typically can comprise oxyethylene units $(C_2H_4O)_y$, oxypropylene units $(C_3H_6O)_y$, oxybutylene units $(C_4H_8O)_y$, or mixtures thereof. Typically, the polyoxyalkylene block comprises oxyethylene units $(C_2H_4O)_y$.

At least one end of each polyoxyalkylene block in Formula I is linked to a siloxane block by a divalent organic group, designated $R^1$. This linkage is determined by the reaction employed to prepare the $(AB)_n$ block silicone polyether copolymer. The divalent organic groups of $R^1$ may be independently selected from divalent hydrocarbons containing 2 to 30 carbons and divalent organofunctional hydrocarbons containing 2 to 30 carbons. Representative, non-limiting examples of such divalent hydrocarbon groups include; ethylene, propylene, butylene, pentylene, hexylene, heptylene, octylene, and the like. Representative, non-limiting examples of such divalent organofunctional hydrocarbons groups include acrylate and methacrylate. Typically, $R^1$ is propylene, (—$CH_2CH_2CH_2$—).

The $(AB)_n$ block silicone polyethers are endblocked. The endblocking unit is also determined by the reaction employed to prepare the $(AB)_n$ block silicone polyether copolymer, which is generally the residual reactive groups of the reactants used. For example, the $(AB)_n$ block silicone polyether copolymers can be prepared by the metal catalyzed hydrosilylation reaction of a diallyl polyether (i.e. an allyl group is present on each molecular terminal end) with a SiH terminated polyorganosiloxane. The resulting $(AB)_n$ block silicone polyether copolymer would have polyoxyalkylene blocks linked to the silicone blocks via a propyleneoxy group (—$CH_2CH_2CH_2O$—), and using a slight molar excess of the allyl polyether would result in an allyl endblock unit (—$CH_2CHCH_2$). Alternative endblock units can result from the addition of other molecules in the reaction employed to prepare the $(AB)_n$ block silicone polyether copolymer that are capable of reacting with the siloxane or polyether block intermediates. For example, the addition of organic compounds having mono-terminated aliphatic unsaturation (such as a mono allyl terminated polyether) will result in the endcapping of the $(AB)_n$ block silicone polyether copolymer with that organic compound. Typically, the endblocking unit of the $(AB)_n$ block silicone polyether is an allyl ether ($CH_2$=$CHCH_2O$—) or allyl polyether.

The molecular weights of the $(AB)_n$ block silicone polyether copolymers will be determined by the number of repeating siloxane and polyoxyalkylene blocks, as indicated by the subscript z in Formula I. Typically, the value of z is such to provide weight average molecular weights ($M_W$) to range from 1,500 to 150,000, alternatively, from 10,000 to 100,000.

The ratio of the silicone block to the polyoxyalkylene block in the $(AB)_n$ SPEs can also be used to identify which structures form vesicles or stable aqueous emulsions. This molecular parameter is expressed by the value of x/(x+y) in Formula I. The value of x/(x+y) can vary from 0.2 to 0.9, or alternatively from 0.4 to 0.9.

The $(AB)_n$ SPEs of the present invention can be prepared by any method known in the art for preparing such block copolymers. Alternatively, the $(AB)_n$ SPEs of the present invention are prepared according the methods described infra.

The present invention further provides a process to prepare an $(AB)_n$ block silicone polyether copolymer comprising reacting;
a) a SiH terminated organopolysiloxane,
b) a polyoxyalkylene having an unsaturated hydrocarbon group at each molecular terminal,
c) a hydrosilylation catalyst,
d) optionally a solvent, e) optionally an organic endblocker compound having a mono-terminally unsaturated hydrocarbon group, wherein the mole ratio of the unsaturated organic groups to SiH in the reaction is at least 1:1.

The SiH terminated organopolysiloxanes useful in the process of the present invention can be represented by the formula M'DM', where "M'" means a siloxane unit of formula $R_2HSiO_{1/2}$, "D" means a siloxane unit of formula $R_2SiO_{2/2}$, where R is independently a monovalent organic group as defined above. Typically, the SiH terminated organopolysiloxane is a dimethylhydrogensiloxy-terminated polydimethylsiloxane having the average formula $Me_2HSiO(Me_2SiO)_x SiHMe_2$, where x is as defined above. SiH terminated organopolysiloxanes and methods for their preparation are well known in the art.

The polyoxyalkylene useful in the process of the present invention may be a polyoxyethylene comprising the average formula —$(C_2H_4O)_y$—, where y is defined as above, and is terminated at each molecular chain end (i.e. alpha and omega positions) with a unsaturated organic group. The unsaturated organic group can be an unsaturated hydrocarbon group such as alkenyl or alkynyl group. Representative, non-limiting examples of the alkenyl groups are shown by the following structures; $H_2C\!=\!CH\!-\!$, $H_2C\!=\!CHCH_2\!-\!$, $H_2C\!=\!C(CH_3)CH_2\!-\!$, $H_2C\!=\!CHCH_2CH_2\!-\!$, $H_2C\!=\!CHCH_2CH_2CH_2\!-\!$, and $H_2C\!=\!CHCH_2CH_2CH_2CH_2\!-\!$. Representative, non-limiting examples of alkynyl groups are shown by the following structures; $HC\!\equiv\!C\!-\!$, $HC\!\equiv\!CCH_2\!-\!$, $HC\!\equiv\!CC(CH_3)\!-\!$, $HC\!\equiv\!CC(CH_3)_2\!-\!$, $HC\!\equiv\!CC(CH_3)_2CH_2\!-\!$. Polyoxyethylenes having an unsaturated hydrocarbon group at each molecular terminal are known in the art, and many are commercially available. Alternatively, the unsaturated organic group can be an organofunctional hydrocarbon such as an acrylate, methacrylate and the like. Typically the polyoxyethylene has the average formula $H_2C\!=\!CHCH_2O(CH_2CH_2O)_yCH_2CH\!=\!CH_2$ wherein y is greater than 4, or alternatively ranges from range from 5 to 30, or alternatively from 5 to 22.

The SiH terminated organopolysiloxane and polyoxyalkylene having an unsaturated organic group at each molecular terminal are reacted in the presence of a hydrosilylation catalyst, which are known in the art. Such hydrosilylation catalysts are illustrated by any metal-containing catalyst which facilitates the reaction of silicon-bonded hydrogen atoms of the SiH terminated organopolysiloxane with the unsaturated hydrocarbon group on the polyoxyethylene. The metals are illustrated by ruthenium, rhodium, palladium, osmium, iridium, or platinum.

Hydrosilylation catalysts are illustrated by the following; chloroplatinic acid, alcohol modified chloroplatinic acids, olefin complexes of chloroplatinic acid, complexes of chloroplatinic acid and divinyltetramethyldisiloxane, fine platinum particles adsorbed on carbon carriers, platinum supported on metal oxide carriers such as $Pt(Al_2O_3)$, platinum black, platinum acetylacetonate, platinum(divinyltetramethyldisiloxane), platinous halides exemplified by $PtCl_2$, $PtCl_4$, $Pt(CN)_2$, complexes of platinous halides with unsaturated compounds exemplified by ethylene, propylene, and organovinylsiloxanes, styrene hexamethyldiplatinun, and $RhCl_3(Bu_2S)_3$.

The amount of hydrosilylation catalyst that is used is not narrowly limited as long as there is a sufficient amount to accelerate a reaction between the polyoxyethylene having an unsaturated hydrocarbon group at each molecular terminal and the SiH terminated organopolysiloxane at room temperature or at temperatures above room temperature. The exact necessary amount of this catalyst will depend on the particular catalyst utilized and is not easily predictable. However, for platinum-containing catalysts the amount can be as low as one weight part of platinum for every one million weight parts of components the polyoxyethylene having an unsaturated hydrocarbon group at each molecular terminal and the SiH terminated organopolysiloxane. The catalyst can be added at an amount 10 to 120 weight parts per one million parts of components the polyoxyethylene having an unsaturated organic group at each molecular terminal and the SiH terminated organopolysiloxane, but is typically added in an amount from 10 to 60 weight parts per one million parts of the polyoxyethylene having an unsaturated organic group at each molecular terminal and the SiH terminated organopolysiloxane.

The hydrosilylation reaction can be conducted neat or in the presence of d), a solvent. The solvent can be an alcohol such as methanol, ethanol, isopropanol, butanol, or n-propanol, a ketone such as acetone, methylethyl ketone, or methyl isobutyl ketone; an aromatic hydrocarbon such as benzene, toluene, or xylene; an aliphatic hydrocarbon such as heptane, hexane, or octane; a glycol ether such as propylene glycol methyl ether, dipropylene glycol methyl ether, propylene glycol n-butyl ether, propylene glycol n-propyl ether, or ethylene glycol n-butyl ether, a halogenated hydrocarbon such as dichloromethane, 1,1,1-trichloroethane or methylene chloride, chloroform, dimethyl sulfoxide, dimethyl formamide, acetonitrile, tetrahydrofuran, white spirits, mineral spirits, or naphtha.

The amount of solvent can be up to 50 weight percent, but is typically from 20 to 50 weight percent, said weight percent being based on the total weight of components in the hydrosilylation reaction. The solvent used during the hydrosilylation reaction can be subsequently removed from the resulting silicone polyether by various known methods.

Additional components can be added to the hydrosilylation reaction which are known to enhance such reactions. These components include salts such as sodium acetate which have a buffering effect in combination with platinum catalysts.

In a first embodiment of the present invention, the $(AB)_n$ SPEs of Formula I have a value of x (i.e. the degree of polymerization, DP, of the polysiloxane chain in the siloxane units) that ranges from 20 to 100, alternatively from 30 to 75. These structures form vesicles in aqueous media. Such vesicle compositions can be prepared by mixing the $(AB)_n$ SPEs with water using any technique known common in the state of the art for creating vesicle compositions. The type and extent of the mixing technique will depend on the specific structure of the $(AB)_n$ SPE chosen. For example, some $(AB)_n$ SPEs will form vesicle compositions spontaneously when mixed with water, while others $(AB)_n$ SPEs will require the presence of an optional water soluble solvent (Component B described infra) to facilitate the formation of vesicles.

Optional component B) is a water-miscible volatile solvent. As used herein "water-miscible" means the solvent forms a dispersion with water at room temperature for at least several hours. "Volatile" means the solvent has a higher vapor pressure than water at various temperatures. As such, when the aqueous dispersion of the organopolysiloxane and solvent are subjected to conditions to remove the solvent, such as heating the dispersion under reduced pressures, the solvent is primarily removed first, allowing all or most of the water to remain in the composition.

Suitable water-miscible volatile solvents as component B) include organic solvents such as alcohols, ethers, glycols, esters, acids, halogenated hydrocarbons, diols. The organic solvents should be miscible with water at the proportion and lower in order to effectively disperse silicones and maintain stable and uniform dispersion overtime. For the purpose of illustration, water-miscible alcohols include methanol, ethanol, propanol, isopropanol, butanol, and higher hydrocarbon alcohols; ethers include gylcol ethers, methyl-ethyl ether, methyl isobutyl ether (MIBK), etc; glycols include propylene glycols, esters include esters of triglycerol, the esterification products of acid and alcohol; halogenated hydrocarbons include chloroform. Typically water-miscible organic solvents are solvents with relatively low boiling points (<100° C.) or high evaporation rate, so they may be removed under vacuum with ease. The most preferred water-miscible organic solvents for this invention are volatile alcohols including methanol, ethanol, isopropanol, and propanol. These alcohols can be removed from aqueous mixtures containing silicone dispersions via vacuum stripping at ambient temperature.

The aqueous compositions may further optionally comprise a silicone or organic oil, component C). The silicone can be any organopolysiloxane having the general formula $R_rSiO_{(4-i)/2}$ in which i has an average value of one to three and R is a monovalent organic group. The organopolysiloxane can be cyclic, linear, branched, and mixtures thereof.

Component C) may be a volatile methyl siloxane (VMS) which includes low molecular weight linear and cyclic volatile methyl siloxanes. Volatile methyl siloxanes conforming to the CTFA definition of cyclomethicones are considered to be within the definition of low molecular weight siloxane.

When component C) is an organic oil, it may be selected from any organic oil known in the art suitable for use in the preparation of personal, household, or healthcare formulations. Suitable organic oils include, but are not limited to, natural oils such as coconut oil; hydrocarbons such as mineral oil and hydrogenated polyisobutene; fatty alcohols such as octyldodecanol; esters such as C12-C15 alkyl benzoate; diesters such as propylene dipelarganate; and triesters, such as glyceryl trioctanoate. The organic oil components can also be mixture of low viscosity and high viscosity oils. Suitable low viscosity oils have a viscosity of 5 to 100 mPa·s at 25° C., and are generally esters having the structure RCO—OR' wherein RCO represents the carboxylic acid radical and wherein OR' is an alcohol residue. Examples of these low viscosity oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or mixtures of octyldodecanol, acetylated lanolin alcohol, cetyl acetate, isododecanol, polyglyceryl-3-diisostearate, or mixtures thereof. The high viscosity surface oils generally have a viscosity of 200-1,000,000 mPa·s at 25° C., preferably a viscosity of 100,000-250,000 mPa·s. Surface oils include castor oil, lanolin and lanolin derivatives, triisocetyl citrate, sorbitan sesquioleate, C10-18 triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or mixtures thereof. Mention may be made, among the optional other non-silicone fatty substances, of mineral oils, such as liquid paraffin or liquid petroleum, of animal oils, such as perhydrosqualene or arara oil, or alternatively of vegetable oils, such as sweet almond, calophyllum, palm, castor, avocado, jojaba, olive or cereal germ oil. It is also possible to use esters of lanolic acid, of oleic acid, of lauric acid, of stearic acid or of myristic acid, for example; alcohols, such as oleyl alcohol, linoleyl or linolenyl alcohol, isostearyl alcohol or octyldodecanol; or acetylglycerides, octanoates, decanoates or ricinoleates of alcohols or of polyalcohols. It is alternatively possible to use hydrogenated oils which are solid at 25° C., such as hydrogenated castor, palm or coconut oils, or hydrogenated tallow; mono-, di-, tri- or sucroglycerides; lanolins; or fatty esters which are solid at 25° C.

The formation of vesicles in the compositions of the present invention can be confirmed by techniques common in the state of the art. Typically, vesicles having a lamellar phase structure which exhibit birefringence when examined with a cross polarizing microscope. Alternatively, the formation of vesicles can be demonstrated by Cyro-Transmission Electron Microscopy (Cryo-TEM) techniques. Particle size measurements can also be used to indicate that the organopolysiloxanes are sufficiently dispersed in aqueous medium typical of vesicle sizes For example, average particle sizes of less than 0.500 μm (micrometers), are typical for dispersed vesicles. Vesicles having a average particle size of less than 0.200 μm, or 0.100 μm are possible with the teachings of the present invention.

The amount of the $(AB)_n$ block silicone polyether copolymer (Component A), optional water-miscible volatile solvent (Component B), and water can vary in the compositions of the present invention, but typically range as follows;

A) 2 to 50 wt %, alternatively 2 to 25 wt %, or alternatively 2 to 15 wt %,

B) 0 to 50 wt %, alternatively 2 to 30 wt %, or alternatively 2 to 20 wt %,

C) 0 to 50 wt %, alternatively 1 to 20 wt %, or alternatively 2 to 10 wt %, and sufficient amounts of water to provide the sum of the wt % of A), B), and water to equal 100%.

Alternatively, the vesicle compositions can be prepared according to the methods of the present invention, as discussed infra.

The present invention also provides a process for making an aqueous composition comprising;

I) combining,
A) an $(AB)_n$ block silicone polyether copolymer having the average formula;

—$[R^1(R_2SiO)_x(R_2SiR^1O)(C_mH_{2m}O)_y]_z$— where x and y are greater than 4, m is from 2 to 4 inclusive,
z is greater than 2,
R is independently a monovalent organic group,
$R^1$ is a divalent hydrocarbon containing 2 to 30 carbons, B) an optional water miscible volatile solvent,
with water to form an aqueous dispersion, II) mixing the aqueous dispersion to form dispersed particles of the $(AB)_n$ silicone polyether copolymer having an average particle size of less than 10 micrometers, III) optionally, removing the water miscible volatile solvent from the aqueous dispersion.

Step I) involves combining an $(AB)_n$ SPEs, component A) and optional component B), a water-miscible volatile solvent. Components A) and B) in step I) are the same as described above. The amount of components A), B), and water combined in step I) can vary in the process, but typically range as follows;

A) 2 to 50 wt %, alternatively 2 to 25 wt %, or alternatively 2 to 15 wt %,

B) 0 to 50 wt %, alternatively 2 to 30 wt %, or alternatively 2 to 20 wt %, and sufficient amounts of water to provide the sum of the wt % of A), B), and water to equal 100%.

Step II in the above process is mixing the aqueous dispersion formed in Step I to form dispersed particles of the (AB)$_n$ silicone polyether copolymer having an average particle size of less than 10 micrometers. There are no special requirements or conditions needed to effect the mixing of step II). Mixing techniques can be simple stirring, homogenizing, sonalating, and other mixing techniques known in the art. The mixing can be conducted in a batch, semi-continuous, or continuous process.

Step III in the above process is optional, and involves removing the water miscible volatile solvent, component B). Typically, the water miscible volatile solvent is removed by known techniques in the art, such as subjecting the vesicle composition to reduced pressures, while optionally heating the composition. Devices illustrative of such techniques include rotary evaporators and thin film strippers.

In a second embodiment of the present invention, the (AB)$_n$ SPEs of Formula I have a value of x (i.e. the degree of polymerization, DP, of the polysiloxane chain in the siloxane units) that ranges from 5 to 19, alternatively from 5 to 10. These structures form stable emulsions in aqueous media having a particle size of less than 10 micrometers. The stable emulsions can be prepared by mixing the (AB)$_n$ SPEs of the second embodiment with water. according to known techniques for preparing water continuous emulsions. Alternatively, the emulsion compositions can be prepared according to the methods of the present invention, as discussed infra.

The present invention thus provides a process for preparing a water continuous emulsion having an average particle size of less than 10 micrometers comprising;

I) mixing
A) an (AB)$_n$ block silicone polyether copolymer having the average formula;

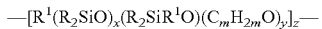

where x and y are greater than 4, m is from 2 to 4 inclusive,
z is greater than 2,
R is independently a monovalent organic group,
R$^1$ is a divalent hydrocarbon containing 2 to 30 carbons,
B) an optional water miscible volatile solvent
to form a hydrophobic phase, II) adding water to the hydrophobic phase to form the water continuous emulsion.

The (AB)$_n$ SPEs, component A) and optional water-miscible volatile solvent, component B) in step II) of the above process are the same as described above.

After forming a hydrophobic phase of A) and B), water is then added to the mixture in step II of the present process to prepare a water continuous emulsion. There are no special requirements or conditions needed for effecting the mixing of components A), B) in step I and subsequent mixing with water in step II). The mixing and water addition steps can be conducted in a batch, semi-continuous, or continuous process.

The hydrophobic phase of step I) can also comprise a silicone or organic oil, as component C), and is the same as described above The hydrophobic phase of step I) can also comprise optionally a personal, household, or healthcare active. A listing of possible personal, household, or health care ingredients is taught in WO 03/101412, which is incorporated herein by reference. The personal or health care ingredient can also be selected from a personal or health care "active", that is, any compound known to have either cosmetic and/or pharmaceutical activity. A representative listing of such personal or health care actives are disclosed in U.S. Pat. No. 6,168,782, which is hereby incorporated by reference. The common assignee's U.S. Pat. No. 5,948,855 (Sep. 7, 1999), also contains an extensive list of some appropriate oil soluble active ingredients such as vitamins and drugs which can be used in the oil phase of the oil in water emulsions, among which are vitamins, including but not limited to, Vitamin A$_1$, RETINOL, C$_2$-C$_{18}$ esters of RETINOL, Vitamin E, TOCOPHEROL, esters of Vitamin E, and mixtures thereof. RETINOL includes trans-RETINOL, 13-cis-RETINOL, 11-cis-RETINOL, 9-cis-RETINOL, and 3,4-didehydro-RETINOL. Other vitamins which are appropriate include RETINYL ACETATE, RETINYL PALMITATE, RETINYL PROPIONATE, α-TOCOPHEROL, TOCOPHERSOLAN, TOCOPHERYL ACETATE, TOCOPHERYL LINOLEATE, TOCOPHERYL NICOTINATE, and TOCOPHERYL SUCCINATE.

The amount of components A), B), C), and D) can vary in the process to prepare the emulsions of the present invention, but typically range as follows;
A) 2 to 60 wt %, alternatively 2 to 50 wt %, or alternatively 2 to 40 wt %,
B) 0 to 50 wt %, alternatively 2 to 30 wt %, or alternatively 2 to 20 wt %,
C) 0 to 30 wt %, alternatively 0 to 25 wt %, or alternatively 0 to 20 wt %,
D) 0 to 30 wt %, alternatively 0 to 25 wt %, or alternatively 0 to 20 wt %, where sufficient amount of water is added to provide the sum of the wt % of A), B), C), D), and water to equal 100%.

The present invention also relates to vesicle compositions further comprising a personal, household, or health care ingredient. Thus, the vesicle compositions can be used to entrap, and subsequently deliver after application, a personal, household care, or health care ingredient. A listing of possible personal, household, or health care ingredients is taught in WO 03/101412, which is incorporated herein by reference. The personal or health care ingredient can also be selected from a personal or health care "active", that is, any compound known to have either cosmetic and/or pharmaceutical activity. A representative listing of such personal or health care actives are disclosed in U.S. Pat. No. 6,168,782, which is hereby incorporated by reference.

Compositions prepared according to the invention can be used in various over-the-counter (OTC) personal care compositions, health care compositions, and household care compositions, but especially in the personal care arena. Thus, they can be used in antiperspirants, deodorants, skin creams, skin care lotions, moisturizers, facial treatments such as acne or wrinkle removers, personal and facial cleansers, bath oils, perfumes, colognes, sachets, sunscreens, pre-shave and after-shave lotions, liquid soaps, shaving soaps, shaving lathers, hair shampoos, hair conditioners, hair sprays, mousses, permanents, depilatories, hair cuticle coats, make-ups, color cosmetics, foundations, blushes, lipsticks, lip balms, eyeliners, mascaras, oil removers, color cosmetic removers, nail polishes, and powders.

EXAMPLES

The following examples are presented to further illustrate the compositions and methods of this invention, but are not to be construed as limiting the invention. All parts and percentages in the examples are on a weight basis and all measurements were obtained at 23° C., unless indicated to the contrary.

Materials

The representative $(AB)_n$ silicone polyethers, herein designated as $(AB)_n$ SPE, used in the emulsion compositions of the present invention were prepared from the hydrosilylation reaction of M'D$_x$M' siloxanes (dimethyl-hydrogen terminated (Me$_2$HSiO) linear polydimethylsiloxanes of varying degree of polymerizations (as designated by x and prepared using well known siloxane polymerization techniques) and allyl terminated polyethers (alpha, omega-diallyloxy polyethers having the average formula, (CH$_2$=CHCH$_2$O(CH$_2$CH$_2$O)$_m$CH$_2$CH=CH$_2$).

Polyglycol AA600, AA1200, and AA2000 were used as obtained from Clariant (Mt. Holly, N.C.), and contained on average 12, 25, and 44 ethylene oxide units (designated as EO, i.e. m=12, 25, and 44 in the above formula).

Testing Procedures

Particle Size

Cyro-Transmission Electron Microscopy (TEM)

The vesicle compositions were analyzed via Cyro-TEM techniques according to the following procedure. Around 2.3 µl of aqueous sample solution was loaded using a micropipette on a lacey carbon film coated Cu TEM grid that was cleaned and rinsed with acetone and chloroform. The samples were diluted to 5% solution with de-ionized water. The excess fluid on the grid surface was removed by blotting the surface with a filter paper for 1.5 second to make an aqueous thin film for TEM. The grid was then plunged into a liquid ethane contained in a small vessel located in a larger liquid nitrogen vessel under −175° C. atmosphere in the cryo-plunge system to vitrify the water film on the grid and to avoid water crystallization. The quenched sample grid was transferred in to the cryo-grid box in the cryo-plunge system. The grid box containing the sample was transferred into a Gatan cryo-transfer system filled with liquid nitrogen and loaded in a cryo-TEM stage, which has been positioned in the cryo-transfer system and cooled down to below −160° C. The sample was loaded in TEM (JEOL 2000FX) and the images were observed at below −160° C. A much colder finger, cooled to −180° C. in TEM using liquid nitrogen, was present to reduce any possible contamination on the cold specimen surface under high vacuum during TEM analysis. The digital images, as shown herein, were taken using a Gatan CCD camera attached at the bottom of the TEM column and Digital Micrograph software.

Examples 1-6

Reference

Various $(AB)_n$ SPEs, as summarized in Tables 1 were prepared via the platinum catalyzed hydrosilylation of the SiH siloxanes with the allyl polyethers utilizing the following general procedure.

Procedure to Prepare SPEs

A 1000 ml three neck round bottom flash equipped with temperature probe, electrical stirrer, and condenser was charged with an amount (as indicated in Table 1) of a polyethylene glycol diallyl ether (Clariant Corp., Mt. Holly, N.C.), 61 gram of xylene and 0.28 gram of sodium acetate. The contents of the flask were then heated to 100° C. A dimethylhydrogen endblocked polydimethyl siloxane was added dropwise via an addition funnel (amount and structures shown in Table 2). After adding 5 gram of the siloxane, 0.60 gram of platinum catalyst (1,3-diethenyl-1,1,3,3-tetramethyldisiloxane platinum complex in dimethyl siloxane) was added to the mixture. When half of the siloxane was added, an additional 0.69 gram of Pt catalyst was added, followed by 0.71 gram of Pt when all the siloxane addition was complete. The reaction mixture was allowed to mix for 1 hour for the polymer to grow. The xylene solvent was then removed via vacuum stripping at 150° C.

Multiple batches of $(AB)_n$ SPEs block copolymers were made, in some cases, to create molecular weight variations of the same $(AB)_n$ SPEs block copolymers from a given siloxane and polyether combinations. These also demonstrate the suitability of $(AB)_n$ copolymers having different chain lengths (i.e. n values) to prepare the vesicle compositions.

TABLE 1

| SPE Example Reference # | Siloxane block | Siloxane used (g) | Polyether used | Polyether used (g) | $M_W$ |
|---|---|---|---|---|---|
| $(AB)_n$ SPE 1 | M'D$_{30}$M' | 180.7 | AA1200 | 119.33 | 19,486 |
| $(AB)_n$ SPE 2 | M'D$_{50}$M' | 394.3 | AA1200 | 105.78 | 50,108 |
| $(AB)_n$ SPE 3A | M'D$_{75}$M' | 850.1 | AA1200 | 149.26 | 40,158 |
| $(AB)_n$ SPE 3B | M'D$_{75}$M' | 850.1 | AA1200 | 180.0 | 44,885 |
| $(AB)_n$ SPE 4 | M'D$_{100}$M' | 223.1 | AA1200 | 25.0 | 88,800 |
| $(AB)_n$ SPE 5 | M'D$_{50}$M' | 161.4 | AA2000 | 88.7 | 22,306 |

Examples 12-16

Vesicle Compositions from $(AB)_n$ SPE 2

The following procedure was used to prepare the vesicle compositions summarized in Table 3 as Examples 12 and 13.

Isopropanol (IPA) was added to $(AB)_n$ SPE 2, (a $(AB)_n$ block copolymer of M'D$_{50}$M' siloxane and polyglycol AA1200 polyether, having a weight-average molecular weight Mw of 50,108 g/mole), to provide a homogeneous mixture. With continuous mixing, water was added slowly to form a homogeneous dispersion having an average particle size of 0.208 µm. The IPA in the dispersion was then removed using a Rotovapor under vacuum at ambient temperature, to yield an alcohol-free, homogeneous dispersion having an average particle size of 0.223 µm, designated as Example 13.

Three additional vesicle compositions using (AB)n SPE 2 block copolymer were made, following the procedure of Example 12, except an optional homogenization step was introduced after the mixture was made and before the vacuum strip. Ethanol (EtOH) was used in place of IPA as the alcohol. The compositions are summarized in Table 3. As the data indicates, the homogenization step reduced the average particle size and maintained the homogeneity of the dispersion. Removal of the volatile alcohol (EtOH) did not compromise the quality of the dispersion.

The particle size distributions of the compositions for Example 14-16 are shown in FIG. 1. The cyro TEM images of the compositions of Examples 13-16, as shown in FIGS. 2-5, confirm the presence of the vesicle structures.

TABLE 3

| | Example # Experiment # | | | | |
|---|---|---|---|---|---|
| | 12 | 13 | 14 | 15 | 16 |
| Process History | Mixed | Mixed, then stripped | Mixed | Mixed, homogenized | Mixed, homogenized, then stripped |
| Alcohol type | IPA | IPA | EtOH | EtOH | EtOH |
| (AB)$_n$ SPE 2, g | 30.27 | 22.35 | 30.25 | 30.25 | 16.30 |
| Alcohol, g | 90.41 | 66.73 | 90.98 | 90.98 | 49.01 |
| Water | 180.78 | 133.44 | 180.06 | 180.06 | 97.00 |
| Batch size, as mixed | 301.46 | 222.52 | 301.29 | 301.29 | 162.31 |
| Alcohol Removed | | −62.40 | | | −46.90 |
| Batch size, after strip | | 160.12 | | | 115.41 |
| | Final composition | | | | |
| Wt. % Polymer | 10.0 | 14.0 | 10.04 | 10.04 | 14.12 |
| Wt. % alcohol | 30.0 | 2.7 | 30.20 | 30.20 | 1.83 |
| Wt. % Water | 60.0 | 83.3 | 59.76 | 59.76 | 84.05 |
| Avg. particle size, μm | 0.2081 | 0.2235 | 0.387 | 0.1388 | 0.175 |
| D(v, 0.5), μm | 0.1003 | 0.085 | 0.2556 | 0.1023 | 0.1474 |
| D(v, 0.9), μm | 0.552 | 0.828 | 0.912 | 0.2872 | 0.321 |

Examples 17-19

Vesicle Compositions from (AB)$_n$ SPE 1

Vesicle compositions of (AB)$_n$ SPE 1 an (AB)$_n$ block copolymer of M'D$_{30}$M' siloxane and polyglycol AA1200 polyether, having a weight-average molecular weight Mw of 19486 g/mole were prepared following the procedure of Examples 12-13. These vesicle compositions are summarized in Table 4 as Examples 17-19. All three compositions had an average particle size distribution of less than 40 nm (0.040 μm). These examples demonstrate that the removal of alcohol did not affect the quality of dispersion and the homogenization step is optional.

TABLE 4

| | Example # | | |
|---|---|---|---|
| | 17 | 18 | 19 |
| Process History | Mixed | Mixed, homogenized | Mixed, homogenized, stripped |
| 19162-20 (AB)n SPE 1, g | 30.04 | 30.040 | 18.13 |
| EtOH, g | 90.41 | 90.410 | 54.40 |
| Water, g | 181.02 | 181.020 | 108.80 |
| Batch size, as mixed, g | 301.47 | 301.47 | 181.34 |
| EtOH Removed | | | −66.6 |
| Batch size, after strip, g | | | 114.7 |

TABLE 4-continued

| | Example # | | |
|---|---|---|---|
| | 17 | 18 | 19 |
| Final dispersion composition | | | |
| Wt. % SPE | 10.0 | 10.0 | 15.8 |
| Wt. % EtOH | 30.0 | 30.0 | 0.0 |
| Wt. % Water | 60.0 | 60.0 | 84.2 |
| Appearance | Almost clear dispersion | Almost clear dispersion | Hazy uniform dispersion |
| Avg. particle size, μm | 0.023 | 0.039 | 0.030 |
| D(V, 0.5), μm | 0.022 | 0.027 | 0.023 |
| D(v, 0.9), μm | 0.034 | 0.080 | 0.057 |

Examples 20-23

Vesicle Compositions from (AB)$_n$ SPE 3 A & B

Vesicle compositions were prepared from (AB)$_n$ SPE 3 A and B, (AB)n silicone polyether block copolymers of M'D$_{75}$M' siloxane and polyglycol AA1200 polyether having a weight-average molecular weight Mw of 40, 158 and 44,885 g/mole, respectively. These dispersions were made following the procedure described in Examples 12-13 and are summarized in Table 5.

TABLE 5

| | ID example | | | |
|---|---|---|---|---|
| | 20 | 21 | 22 | 23 |
| Process History | Mixed | Mixed | Mixed | Mixed |
| 19162-56 (AB)n SPE, g | 2.022 | 2.038 | | |
| 19162-57 (AB)n SPE, g | | | 2.092 | 2.097 |
| IPA, g | 9.082 | | 9.011 | |

TABLE 5-continued

| | ID example | | | |
|---|---|---|---|---|
| | 20 | 21 | 22 | 23 |
| EtOH, g | | 9.079 | | 9.065 |
| Water, g | 9.016 | 9.123 | 9.096 | 9.106 |
| Dispersion Composition | | | | |
| Wt. % SPE | 10.0 | 10.1 | 10.4 | 10.3 |
| Wt. % Alcohol | 45.1 | 44.9 | 44.6 | 44.7 |
| Wt. % Water | 44.8 | 45.1 | 45.0 | 44.9 |
| Appearance | Cloudy, homogeneous dispersion | Cloudy, homogeneous dispersion | Cloudy, homogeneous dispersion | Cloudy, homogeneous dispersion |
| Avg. particle size, um | 0.740 | 0.167 | 1.715 | 0.189 |
| D(v, 0.5), um | 0.660 | 0.138 | 1.637 | 0.142 |
| D(v, 0.9), um | 1.642 | 0.311 | 2.655 | 0.396 |

Examples 24-25

Alcohol Free Vesicle Compositions from $(AB)_n$ SPE 3 B

Alcohol-free vesicle compositions were prepared from $(AB)_n$ SPE 3 B an (AB)n silicone polyether block copolymer of $M'D_{75}M'$ siloxane and polyglycol AA1200 polyether, having a weight-average molecular weight Mw of 44,885 g/mole following the procedure of Examples 12-13, and removing the alcohol under reduced pressure. The compositions are summarized in Table 6.

TABLE 6

| | ID example | |
|---|---|---|
| | 24 | 25 |
| Process History | Mixed | Mixed, stripped |
| (AB)n SPE 3B, g | 30.820 | 27.783 |
| IPA, g | 120.470 | 108.597 |
| Water, g | 150.980 | 136.100 |
| Batch size, as mixed | 302.27 | 272.48 |
| IPA Removed | | −100.5 |
| Batch size, stripped | | 172.0 |
| Dispersion composition | | |
| Wt. % SPE | 10.20 | 16.15 |
| Wt. % IPA | 39.86 | 4.71 |
| Wt. % Water | 49.95 | 79.14 |
| Appearance | Hazy to slight cloudy; homogeneous | Milky opaque, uniform dispersion |
| Avg. particle size, um | 0.604 | 0.784 |
| D(v, 0.5), um | 0.523 | 0.397 |
| D(v, 0.9), um | 1.064 | 0.779 |

Example 26-27

Vitamin A Palmitate Loaded in Vesicles from (AB)n SPE 1

Vitamin A palmitate was first mixed with isopropanol at 50/50 ratio. The vitamin/IPA mixture was then mixed with (AB)n SPE 1, a (AB)n block copolymer of $M'D_{30}M'$ siloxane and polyglycol AA1200 polyether, having a weight-average molecular weight Mw of 19486 g/mole to homogenous. Ethanol was then admixed to form a homogeneous mixture. While under continuous mixing, de-ionized water was slowly and gradually incorporated into the SPE/vitamin/alcohol mixture, till homogenous. The mixture was homogenized, using an APV-2000 Gaulin homogenizer, producing a homogeneous dispersion with sub-micron particle size, identified as Example 26 in Table 8. The Example 26 composition was then further homogenized. The alcohol was removed under reduced pressure at ambient temperature to produce a composition having an average particle size of 0.54 um, listed as Example 27 in Table 8. The removal of alcohol processing aid did not affect the dispersion quality and the particle size.

TABLE 8

| | Example# | |
|---|---|---|
| | 26 | 27 |
| Process History | Mixed, homogenized | Mixed, homogenized, and stripped |
| Vitamin A palmitate, g | 6.65 | 4.69 |
| IPA, g | 6.65 | 4.58 |
| EtOH, g | 90.86 | 62.88 |
| (AB)n SPE 1, g | 30.17 | 20.88 |
| D.I. Water, g | 180.15 | 124.65 |
| Batch size, as mixed | 314.48 | 217.62 |
| Alcohol removed, g | | −60.1 |
| Batch size, after strip | | 157.52 |
| Final dispersion composition | | |
| Wt. % VAP | 2.11 | 2.91 |
| Wt. % Polymer | 9.59 | 13.25 |
| Wt. % Alcohol | 31.05 | 4.73 |
| Wt. % Water | 57.28 | 79.11 |
| Appearance | Milky yellow liquid | Milky yellow liquid |
| Avg. particle size, μm | 0.540 | 0.574 |
| D(v, 0.5), μm | 0.358 | 0.353 |
| D(v, 0.9), μm | 1.231 | 1.266 |

Example 28

The following vitamin A palmitate loaded (AB)n SPE vesicles in water dispersion was prepared according to the method shown in the previous examples of this invention. The (AB)n SPE is a copolymer of 50 dp siloxane and Polyglycol AA1200 polyether. The final composition of the vesicle dispersion is shown in Table 9.

TABLE 9

| Example # 28 | |
|---|---|
| (AB)n SPE, g | 118.00 |
| Vitamin Premix | 35.38 |
| Vit A Palmitate in the premix, g | 25.16 |
| D.I. Water, g | 346.62 |
| Wt. % SPE Polymer | 23.60 |
| Wt. % VAP | 5.03 |
| Wt. % Tocopherol | 0.51 |
| Wt. % Silicone fluid | 1.28 |
| Wt. % Water | 69.32 |
| Appearance | Beige, milky dispersion, smooth |
| pH of the vesicle dispersion | 5.39 |
| Avg. vesicle size, μm | 0.2583 |

The vitamin-loaded SPE vesicles can easily be formulated into skin care formulations. Oil-based vitamins can be easily incorporated into water-based formulations. The following examples provide such illustrations.

Example 29

Oil-in-Water Body Lotion

| Ingredients | Parts |
|---|---|
| Part A | |
| Cetearyl Alcohol | 3 |
| Diisopropyl Adipate (Crodamol DA) | 5 |
| Dimethicone (Dow Corning Silicone 200/100 cstks) | 0.5 |
| Potassium cetyl phosphate | 1.5 |
| Buthylated hydroxytoluene | 0.05 |
| Cheating agent (EDTA) | 0.1 |
| Phenoxyethanol | 0.6 |
| Part B | |
| Water | up to 100 |
| Carbomer 980 thickener | 30 |
| Potassium hydroxyde | 1.5 |
| Part C | |
| Vitamin A palmitate loaded SPE vesicles | 19.88 |

To prepare the body lotion, the following procedure was followed: The ingredients in Part A were mixed and heated to 85° C. to homogeneous. Cool the part A mixture to 40° C., then incorporate the part B ingredients. Cooled the mixture to ambient temperature. Incorporate vitamin A palmitate-loaded SPE vesicles into the mixture and mix to homogeneous. The final mixture is a smooth, slightly yellowish creamy lotion.

Example 30

Simple Moisturing Gel for Skin

The $(AB)_n$ type SPE vesicles can be easily formulated into aqueous based gel formulations. SPE vesicles provide a convenient means to incorporate oil-soluble vitamins into water-rich gel formulations.

| Ingredients | Parts |
|---|---|
| Part A | |
| Water | to 100% |
| Preservative | 0.30% |
| Polyacrylamide, C13-14 Isoparaffin, laureth-7 (Sepigel 305) | 1% |
| Part B | |
| Vitamin A palmitate-loaded SPE vesicles | 19.88 |

To prepare the gel, the following procedure was followed: The ingredients in Part A were mixed to homogeneous. Vitamin A palmitate-loaded SPE vesicles dispersion was then incorporated and mixed to homogeneous. The final product is a beige, smooth gel.

Figure 6:
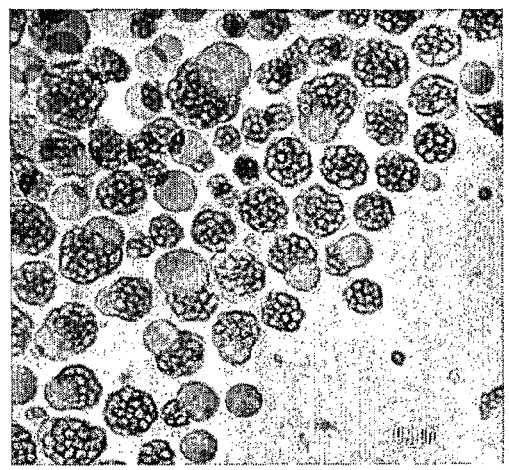

To further demonstrate the integrity of vesicles in formulations, cryo-TEM images of the "as formulated" products were taken. An image of the gel from the above example is shown FIG. 6. As illustrated, the vesicles and aggregates of vesicles were well preserved.

Figure 7:
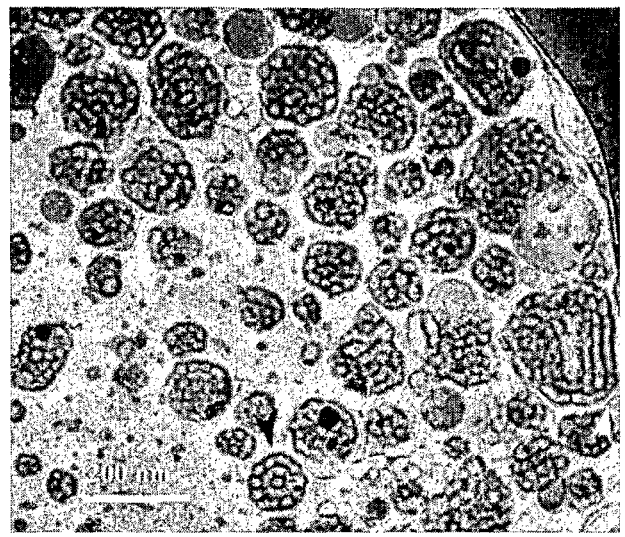

A cryo-TEM image of the "as prepared" body lotion illustrated in Example A, prepared from (AB)n SPE vesicle is shown in FIG. 7. The characteristic vesicles and aggregate structures uniquely associated with the (AB)n SPE vesicles shown in FIG. 7.

Examples 31-32

Reference

A series of $(AB)_n$ SPEs, as listed below, were prepared according to the procedures described in Examples 1-6.

$(AB)_n$ SPE 31A—reaction product from $M'D_{15}M'$ and AA2000, $M_w$=16,022

$(AB)_n$ SPE 31B—reaction product from $M'D_{15}M'$ and AA2000, $M_w$=24,426.

$(AB)_n$ SPE 32A—reaction product from $M'D_{15}M'$ and AA1200, $M_w$=33,552.

$(AB)_n$ SPE 32B—reaction product from $M'D_{15}M'$ and AA1200, $M_w$=35,352.

Example 33

(AB)n SPE 31A Dispersion in Water (AB)n SPE 31A (reaction product of $M'D_{15}M'$ siloxane and polyglycol AA2000 polyether) was a solid, waxy material with a melting point of 45-47° C. A dispersion of this polymer was made by dispersing this solid polymer in water using a low shear mechanical mixing device. The dispersion had an average particle size of 1.867 μm.

Example 34-36

(AB)n SPE 31A Dispersions in Alcohol-Containing Water

Dispersions of (AB)n SPE 31A copolymer were prepared in alcohol-water mixture. The solid (AB)n SPE copolymer was dispersed, via a mechanical shear device, into isopropanol/water mixtures at a ratio of 5/85, and 20/70, respectively, as summarized in Table 10. Additionally, a dispersion of sub-micron size in water was also obtained by vacuum stripping IPA off the mixture.

TABLE 10

| | Example # | | | |
|---|---|---|---|---|
| | 33 | 34 | 35 | 36 |
| Process Process | As mixed | As mixed | As mixed | Mixed, then stripped |
| (AB)n SPE 31A, g | 10.01 | 30.002 | 30.02 | 17.5 |
| IPA, g | | 15.055 | 60.314 | 3.7 |
| D.I. Water, g | 90.68 | 255.106 | 210.305 | 122.5 |
| Final Dispersion Composition | | | | |
| Wt. % Polymer | 10 | 10 | 10 | 12 |
| Wt. % IPA | 0 | 5 | 20 | 3 |
| Wt. % Water | 90 | 85 | 70 | 85 |
| pH of the dispersion | 4.89 | 4.88 | 5.10 | 5.17 |
| Avg. dispersion size, μm | 1.867 | 2.102 | 1.359 | 0.939 |
| D(v, 0.5), μm | 1.316 | 1.635 | 1.344 | 0.303 |
| D(v, 0.9), μm | 4.697 | 4.975 | 2.959 | 2.049 |

Example 37

Vitamin A Palmitate Loaded (AB)n SPE Particle Dispersions

Vitamin A palmitate is not soluble in water and can not be dispersed in water directly. The example shows that particle dispersion forming (AB)n SPE block copolymer can be used to incorporate water-insoluble vitamins and form a stable dispersion in water. The dispersion was prepared as followed: A 50/50 by weight pre-mixture of vitamin A palmitate and Dow Corning® DC 1-2287 vinyl silicone fluid was prepared. The premix was incorporated to form a homogeneous mixture with (AB)n SPE 31A copolymer. Deionized water was slowly incorporated into the above mixture while under continuous mixing. As shown in Table 11, a dispersion having an average particle size of 1.68 μm was obtained in water. The vitamin A palmitate payload in the dispersion particles was 17%.

TABLE 11

| | Example # 37 |
|---|---|
| Process History | Roto-wheel mixed |
| (AB)n SPE 31A, g | 7.681 |
| Vitamin A palmitate, g | 1.64 |
| DC 1-2287 vinyl fluid, g | 1.64 |
| D.I. Water, g | 90.5 |
| Total batch, g | 101.46 |
| Wt. % (AB)n SPE | 7.57 |
| Wt. % VAP | 1.62 |
| Wt. % Vinyl fluid | 1.62 |
| Wt. % Water | 89.20 |
| Avg particle size, μm | 1.676 |
| 50%, μm | 0.8724 |
| 90%, μm | 5.845 |

Examples 38-40

Si/W Emulsions from (AB)n SPE

Three Si/W emulsions of different compositions were prepared via high shear emulsification process. The method of preparation includes the following steps: the silicone fluids were incorporated into (AB)$_n$ SPE 32A copolymer to form a homogeneous mixture. A small amount of water was incorporated into the phase A mixture, followed by high shear mixing to disperse the water using a Speed Mixer. Water additions in small quantity continued until the mixture inverted or form a continuous, smooth cream (called inverted into a water-continuous emulsion concentrate). The remaining water was added to farther dilute the emulsion to desired concentration and consistency. The final emulsions had an average particle size between 1.3 and 2.1 μm.

These Si/W emulsion examples illustrated that it is possible to prepare emulsion particles of desirable compositions comprising the (AB)$_n$ SPE polymer and silicone oils. The compositions are summarized in the Table 12.

TABLE 12

| | Example # | | |
|---|---|---|---|
| | 38 | 39 | 40 |
| Phase A | | | |
| (AB)n SPE 32A (15dp + AA1200), g | 10 | 10 | 20 |
| DC 1-2887 vinyl fluid, g | | 10 | 5 |
| DC 245 fluid, g | 10 | | |
| Phase B | | | |
| D.I. Water, g | 60 | 50 | 61.3 |
| Total batch size, g | 80 | 70 | 86.3 |
| Wt. % (AB)n SPE | 12.50 | 14.29 | 23.17 |
| Wt. % fluid | 12.50 | 14.29 | 5.79 |
| Wt. % water | 75.00 | 71.43 | 71.03 |
| Final appearance: | Smooth, milky white emulsion | Smooth, milky creamy dispersion | Smooth, thick, milky white emulsion |
| Avg. particle size, μm | 2.028 | 1.312 | 1.617 |
| D(v, 0.5), μm | 1.281 | 1.044 | 1.809 |
| D(v, 0.9), μm | 5.06 | 1.925 | 2.851 |

Examples 41-42

Sub-Micron (AB)n SPE 31B Copolymer Particle Emulsions in Water

Another (AB)n SPE block copolymer was used to prepare Si/W emulsions. (AB)n SPE 31B is the block copolymer reaction product of M'D$_{15}$M' siloxane and polyglycol AA2000 polyether (segment length of 44 EO units) and has a melting temperature 45-47° C. These Si/W emulsions Examples were made by mechanical emulsification using a high-shear mixer (Speed Mixer), similar to the ones described above. The step-wise procedures can be found in the previous examples. The final Si/W emulsions had an average particle size of 0.394 μm and 0.725 μm, respectively, as summarized in Table 13.

TABLE 13

| | Example # | |
|---|---|---|
| | 41 | 42 |
| Phase A | | |
| (AB)n SPE 31B, g | 10 | 10 |
| DC 1-2287 vinyl fluid, g | 10 | |
| DC 245 fluid, g | | 10 |

TABLE 13-continued

| | Example # | |
|---|---|---|
| | 41 | 42 |
| Phase B | | |
| D.I. Water, g | 50.3 | 60 |
| Total batch size, g | 70.3 | 80 |
| Wt. % SPE | 14.22 | 12.50 |
| Wt. % fluid | 14.22 | 12.50 |
| Wt. % water | 71.55 | 75.00 |
| Final appearance: | Smooth, thin milky dispersion | Cloudy dispersion with slight creamy feel |
| Avg. particle size, μm | 0.394 | 0.725 |
| D(v, 0.5), μm | 0.296 | 0.619 |
| D(V, 0.9), μm | 0.815 | 1.405 |

Examples 43-45

Si/W Emulsions and Vitamin Loaded (Si+O)/W Emulsions (AB)n SPE block copolymer in Si/W emulsion form can be used to carry and protect water-insoluble oils and substances. These emulsions can subsequently be incorporated into water-based end products and formulations.

Vitamin A palmitate is water-insoluble and cannot be incorporated directly into water-based formulations. These examples showed that stable Si/W emulsions containing various amount of vitamin A palmitate were successfully prepared from (AB)n SPE block copolymer.

The Si/W emulsions were prepared using SPE 32A copolymer, an (AB)n block copolymer product of M'D$_{15}$M' siloxane and polyglycol AA1200 polyether and has a melting temperature of 27-32° C. DC 245 silicone cyclics and DC 1-2287 vinyl silicone fluids were used to prepare the following Si/W and (Si+O)/W emulsions.

These emulsions were prepared following the following procedures: vitamin A palmitate was first mixed with DC 1-2287 vinyl silicone fluid to form a homogeneous mixture, then incorporated into the (AB)n SPE 32A copolymer with mixing to yield a homogeneous premixture. De-ionized water was slowly and gradually incorporated into the phase A mixture using a high-shear mixer (Speed Mixer) till the mixture inverted into water-continuous mixture. The remaining water was added, under shear to complete the dilution to desired composition. The final emulsions are smooth, milky white emulsions, as summarized in Table 14.

The two vitamin A palmitate loaded (AB)n SPE block copolymer emulsions had a particle size of 1.62 μm and 1.02 μm, respectively. The vitamin payload was 13.4% and 20.3%, respectively.

TABLE 14

| | Example # | | |
|---|---|---|---|
| | 43 | 44 | 45 |
| Phase A | | | |
| (AB)n SPE 32A, g | 20 | 20 | 20 |
| DC 1-2287 vinyl fluid, g | 5 | 5.1 | 3.1 |
| Vitamin A palmitate, g | | 3.1 | 5.1 |

TABLE 14-continued

| | Example # | | |
|---|---|---|---|
| | 43 | 44 | 45 |
| Phase B | | | |
| D.I. water, g | 61.3 | 60.8 | 60.9 |
| Batch size, g | 86.3 | 89 | 89.1 |
| Wt. % SPE | 23.17 | 22.47 | 22.45 |
| Wt. % VAP | 0.00 | 3.48 | 5.72 |
| Wt. % fluid | 5.79 | 5.73 | 3.48 |
| Wt. % water | 71.03 | 68.31 | 68.35 |
| Final Dispersion Appearance | Smooth, white creamy emulsion | Smooth, beige emulsion with some viscosity | Smooth, light yellowish emulsion with some viscosity |
| Avg. particle size, μm | 0.369 | 1.617 | 1.021 |
| D(v, 0.5), μm | 0.358 | 1.809 | 0.862 |
| D(v, 0.9), μm | 0.539 | 2.851 | 2.046 |

Examples 46-47

Vitamin Loaded Emulsions Formulated into Skin Care Products

Vitamin A palmitate loaded (AB)n SPE particle dispersions in water were prepared according to the method shown in the previous examples. Example 46 was prepared from (AB)n SPE copolymer of 15 dp silloxane and Polyglycol AA2000 polyether, and Example 47 dispersion from (AB)n SPE copolymer of 15 dp siloxane and Polyglycol AA1200 polyether. The final compositions of these dispersions are shown in Table 15.

TABLE 15

| | Example # | |
|---|---|---|
| | 46 | 47 |
| SPE Polymer type | (AB)n SPE 31B | (AB)n SPE 32B |
| Main SPE structure | 15 dp siloxane & AA2000 polyether | 15 dp siloxane & AA1200 polyether |
| % SPE Polymer | 21.12 | 21.17 |
| Wt. % VAP | 4.23 | 4.24 |
| % Tocopherol | 0.42 | 0.46 |
| % 1-2287 Silicone fluid | 4.23 | 4.25 |
| % Water | 70.00 | 69.89 |
| Appearance of dispersion | Light yellowish, creamy thick paste | Light yellowish, creamy paste |
| PH of dispersion | 5.29 | 3.58 |
| Avg. particle size, μm | 0.326 | 0.355 |

The vitamin-loaded SPE particle dispersions were formulated into skin care formulations.

| Oil-in-water body lotion | |
|---|---|
| Ingredients | Parts |
| Part A | |
| Cetearyl Alcohol | 3 |
| Diisopropyl Adipate (Crodamol DA) | 5 |
| Dimethicone (Dow Corning Silicone 200/100 cs) | 0.5 |
| Potassium cetyl phospate | 1.5 |
| Buthylated hydroxytoluene | 0.05 |
| Cheating agent (EDTA) | 0.1 |

| Oil-in-water body lotion | |
|---|---|
| Ingredients | Parts |
| Phenoxyethanol<br>Part B | 0.6 |
| Water<br>Carbomer 980 thickener<br>Potassium hydroxide<br>Part C | up to 100<br>30<br>1.5 |
| Vitamin A palmitate loaded SPE particle dispersions | 19.88 |

To prepare the body lotion, the following procedure was followed: The ingredients in Part A were mixed and heated to 85° C. to homogeneous. Cool the part A mixture to 40° C., then incorporate the part B ingredients. Cooled the mixture to ambient temperature. Incorporate vitamin A palmitate-loaded SPE particle disperison into the mixture and mix to homogeneous. The final mixture is a smooth, slightly yellowish creamy lotion.

A cryo-TEM image of the "as prepared" body lotion illustrated in this Example confirmed the dispersed particles remained in tack and stable following the preparation of the formulation.

Moisturing Gel for Skin

The (AB)n type SPE particle dispersions can be formulated into aqueous based gel formulations. SPE vesicles provide a convenient means to incorporate oil-soluble vitamins into water-rich gel formulations.

| Ingredients | Parts |
|---|---|
| Part A | |
| Water<br>Preservative<br>Polyacrylamide, C13-14 Isoparaffin,<br>laureth-7 (Sepigel 305)<br>Part B | to 100%<br>0.30%<br>1% |
| Vitamin A palmitate-loaded SPE<br>particle dispersions | 19.88 |

To prepare the gel, the following procedure was followed: The ingredients in Part A were mixed to homogeneous. Vitamin A palmitate-loaded SPE particle dispersion was then incorporated and mixed to homogeneous. The final product is a beige, smooth gel.

To further demonstrate the integrity of the dispersion particles in formulations, cryo-TEM images of the "as formulated" products were taken. The resulting image of the gel from the above example confirmed the dispersion particles were well preserved.

Examples 48-49

The following vitamin A palmitate loaded (AB)n SPE particle dispersions in water were prepared according to the method shown in the previous examples of this invention. An The emulsion labeled as Example 48 was prepared from (AB)n SPE 32A, a copolymer of 15 dp siloxane and Polyglycol AA2000 polyether, and the emulsion labeled as Example 49 from (AB)n SPE 31B, a copolymer of 15 dp siloxane and Polyglycol AA2000 polyether. The final compositions of these dispersions are shown in the following table. In this case, no water-miscible solvent was required. DC 1-2287, a methylvinylsilicone cyclics (from Dow Corning Corp.) was used. The compositions of these two emulsions are shown in Table 16 below.

The stability of the emulsions prepared from (AB)n SPE copolymers are also shown. The particle sizes of these emulsions after 5 weeks aging @ 40° C. were found comparable to their initial values, as illustrated in Table 16.

TABLE 16

| | Example # | |
|---|---|---|
| | 48 | 49 |
| (AB)n SPE type | (AB)n SPE 32A | (AB)n SPE 31 B |
| Carrier Fluid | DC 1-2287 | DC 1-2287 |
| Wt. % (AB)n SPE | 20.13 | 20.31 |
| Wt. % VAP | 4.15 | 4.10 |
| Wt. % silicone fluid | 4.14 | 4.44 |
| Wt. % water | 71.58 | 71.15 |
| Dispersion appearance | Yellow, creamy, uniform emulsion | Yellow uniform emulsion; moderate viscosity |
| Initial particle size, μm | 0.973 | 0.242 |
| Particle size after 5 weeks @ 40 C., μm | 0.965 | 0.398 |

The invention claimed is:

1. A process for making an aqueous composition consisting of;

I) combining,

A) 2 to 50 wt % of an $(AB)_n$ block silicone polyether copolymer having the average formula;

$$-[R^1(R_2SiO)_x(R_2SiR^1O)(C_mH_{2m}O)_y]_z-$$

where x ranges from 30 to 75, y is greater than 4, the value of x/(x+y) ranges from 0.2 to 0.9, m is from 2 to 4 inclusive, z is greater than 2, R is independently a monovalent organic group, $R^1$ is a divalent hydrocarbon containing 2 to 30 carbons, B) 2 to 30 wt % of a water miscible volatile solvent selected from methanol, ethanol, isopropanol, or propanol, with sufficient amounts of water to provide the sum of the wt % of A), B), and water to equal 100% to form an aqueous dispersion, II) mixing the aqueous dispersion to form vesicles of the $(AB)_n$ silicone polyether copolymer having an average particle size of less than 10 micrometers, III) optionally removing the water miscible volatile solvent from the aqueous dispersion.

* * * * *